(12) United States Patent
Tomihara et al.

(10) Patent No.: US 10,086,150 B2
(45) Date of Patent: Oct. 2, 2018

(54) NEEDLE AND METHOD FOR MANUFACTURING THE SAME

(71) Applicant: EFR CO., LTD., Osaka (JP)

(72) Inventors: Akitoshi Tomihara, Osaka (JP); Terumi Takimiya, Osaka (JP); Tetsuo Tanaka, Osaka (JP)

(73) Assignee: EFR CO., LTD., Osaka (JP)

( * ) Notice: Subject to any disclaimer, the term of this patent is extended or adjusted under 35 U.S.C. 154(b) by 208 days.

(21) Appl. No.: 15/032,652

(22) PCT Filed: Oct. 31, 2013

(86) PCT No.: PCT/JP2013/079519
§ 371 (c)(1),
(2) Date: Apr. 28, 2016

(87) PCT Pub. No.: WO2015/063911
PCT Pub. Date: May 7, 2015

(65) Prior Publication Data
US 2016/0310678 A1 Oct. 27, 2016

(51) Int. Cl.
*A61M 5/32* (2006.01)
*C25D 1/02* (2006.01)
(Continued)

(52) U.S. Cl.
CPC ............ *A61M 5/3286* (2013.01); *A61M 5/32* (2013.01); *A61M 5/329* (2013.01); *C25D 1/02* (2013.01);
(Continued)

(58) Field of Classification Search
CPC ...... A61M 5/3286; A61M 5/32; A61M 5/329; A61M 2207/00; A61M 2207/10;
(Continued)

(56) References Cited

U.S. PATENT DOCUMENTS

| 4,869,259 A | * | 9/1989 | Elkins | ................ | A61B 8/0833 |
| | | | | | 600/458 |
| 5,484,423 A | * | 1/1996 | Waskonig | .......... | A61B 17/3401 |
| | | | | | 604/239 |
| 2007/0256289 A1 | | 11/2007 | Tamura et al. | | |

FOREIGN PATENT DOCUMENTS

| JP | 10896/1976 U | 1/1976 |
| JP | H09-279331 A | 10/1997 |

(Continued)

OTHER PUBLICATIONS

International Search Report for PCT/JP2013/079519, dated Feb. 10, 2014.

(Continued)

*Primary Examiner* — Manuel Mendez (57) ABSTRACT

A method for manufacturing a needle tapered along the longitudinal direction by electroforming comprises: a step of immersing a core material (122) having an outer peripheral surface that is tapered along the longitudinal direction in an electrolyte and forming a first electroformed body (126) on an outer peripheral surface (124) of the core material (122); a step of immersing the first electroformed body (126) in an electrolyte to which particles having a prescribed particle size are added and forming a second electroformed body (134) having multiple protrusions (30) on an outer peripheral surface (128) of the first electroformed body (126); a step of cutting the first electroformed body (126) and second electroformed body (134) into a prescribed length and forming a needle (10) having a sharp needle tip (16); and a step of pulling out the core material (122) from the cut first electroformed body (126).

13 Claims, 7 Drawing Sheets

(51) Int. Cl.
    *C25D 5/02*    (2006.01)
    *C25D 15/00*   (2006.01)
    *C25D 1/20*    (2006.01)
    *C25D 3/12*    (2006.01)
    *C25D 5/48*    (2006.01)
    *C25D 9/04*    (2006.01)
    *C25D 5/14*    (2006.01)
    *C25D 3/18*    (2006.01)

(52) U.S. Cl.
    CPC ............... *C25D 1/20* (2013.01); *C25D 3/12* (2013.01); *C25D 5/022* (2013.01); *C25D 5/14* (2013.01); *C25D 5/48* (2013.01); *C25D 9/04* (2013.01); *C25D 15/00* (2013.01); *A61M 2207/00* (2013.01); *C25D 3/18* (2013.01)

(58) Field of Classification Search
    CPC ... C25D 1/02; C25D 1/20; C25D 3/12; C25D 5/022; C25D 5/14; C25D 5/48; C25D 9/04; C25D 15/00
    USPC .................................................. 604/272, 264
    See application file for complete search history.

(56) References Cited

FOREIGN PATENT DOCUMENTS

| | | |
|---|---|---|
| JP | 2005-000611 A | 1/2005 |
| JP | 2006-291345 A | 10/2006 |
| JP | 2007-014428 A | 1/2007 |
| JP | 2007-289664 A | 11/2007 |
| JP | 2008-529711 A | 8/2008 |
| JP | 2008-200528 A | 9/2008 |
| JP | 2012-005576 A | 1/2012 |
| WO | 2006/088288 A1 | 8/2006 |
| WO | 2007/114322 A1 | 10/2007 |
| WO | WO 2013/142988 A1 * | 10/2013 |

OTHER PUBLICATIONS

Written Opinion of the International Searching Authority for PCT/JP2013/079519, dated Feb. 10, 2014.

\* cited by examiner

NEEDLE AND METHOD FOR MANUFACTURING THE SAME

FIELD OF THE INVENTION

The present invention relates to a needle having a tapered shape formed by electroforming, and a method for manufacturing the same.

BACKGROUND OF THE ART

A tool that punctures a living body with a needle is used to inject a liquid medicine into the living body, or extract a body fluid of the living body. When the needle attached to such a tool has a large external diameter, it is said that large pain is caused because a resistance force from the living body increases. For this reason, painless needles have been developed with the external diameter of the needles formed as thin as possible in order to reduce the pain.

In this case, because the needles formed in a thin shape have a small internal diameter, for example, the needles have a large flow resistance during injection of a liquid medicine into the living body. For this reason, a tapered needle has been presented (see Patent Literature 1). The tapered needle has a needle proximal portion having a diameter larger than the diameter of a needle distal portion, to reduce the flow resistance.

For example, the conventional tapered painless needles are formed with a thin external diameter, by rolling up a stainless plate material or elongating a stainless cylindrical member. However, in the case of a needle formed by rolling up a plate material, the joined portion of the rolled plate material needs to be processed with high accuracy. In addition, in the case of a needle formed by elongating a cylindrical member, rust due to the elongation may occur on the internal peripheral surface, and therefore the processing is very difficult. Accordingly, manufacturing of these needles requires much time and great cost.

To solve the above problems, a method for forming a needle by electroforming has been presented (Patent Literatures 2 and 3). In the method, a core material having a diameter corresponding to a passage of the needle is immersed in an electrolyte, an electroformed member is formed on an external peripheral surface of the core material, thereafter the core material is pulled out of the electroformed member, and an end portion of the electroformed member is ground to have an acute angle.

REFERENCE OF THE PRIOR ART

Patent Reference 1: Japanese Patent Application Publication No. 2008-200528
Patent Reference 2: Japanese Patent Application Publication No. 2012-5576
Patent Reference 3: Japanese Patent Application Publication No. 2006-291345

DISCLOSURE OF THE INVENTION

Problems the Invention is Intended to Solve

However, even with a thin needle formed by electroforming, the pain felt by the living body is not sufficiently reduced. For example, the human body has 100 to 200 pain spots per square centimeter as sensory regions to sense pain. Pain occurs by stimulation of pain spots with the needle. The probability that the needle stimulates the pain spot is reduced by reducing the external diameter of the needle. However, even with the very small external diameter, occurrence of pain is not entirely avoided, because the external peripheral surface can contact the pain spots when the needle is caused to puncture and be inserted into the body.

An object of the present invention is to provide a needle that reduces pain during puncture, has small flow distance in a needle tube passage, and can be manufactured with high accuracy at low cost, and a method for manufacturing the same.

SUMMARY OF THE INVENTION

In accordance with an aspect of the present invention, a needle comprises a needle tube formed by electroforming and having a tapered shape along a longitudinal direction, the needle tube being provided with a plurality of projections formed by electroforming on an external peripheral surface of the needle tube, the projections having intervals of 0.2 to 100 μm between adjacent top portions thereof, and a height of 0.1 to 50 μm from the external peripheral surface.

In the needle, projections include particles including at least one selected from the group consisting of silicon carbide, sapphire, diamond, and alumina ceramics.

In the needle, the tapered shape is a curved shape along the longitudinal direction.

In the needle, the tapered shape is a straight shape along the longitudinal direction.

In the needle, the needle is an injection needle.

In accordance with an aspect of the present invention, a method for manufacturing a needle having a tapered shape along a longitudinal direction by electroforming, the method comprise a step of immersing a core material including an external peripheral surface having a tapered shape along the longitudinal direction in an electrolyte, to form a first electroformed member on the external peripheral surface of the core material;

a step of immersing the first electroformed member in an electrolyte to which particles of a certain grain size are added, to form a second electroformed member including a plurality of projections on the external peripheral surface of the first electroformed member;

a step of cutting the first electroformed member and the second electroformed member into a predetermined length, to form a needle including a needle distal portion in an acute-angled shape; and a step of extracting the core material from the cut first electroformed member.

In the method for manufacturing the needle, the method for manufacturing the needle comprises:

a step of applying a masking agent at predetermined intervals on the external peripheral surface of the first electroformed member along the longitudinal direction of the first electroformed member, after the first electroformed member is formed, wherein in the step of forming the second electroformed member, the second electroformed member is formed on the external peripheral surface of the first electroformed member on which the masking agent is not applied, and in the step of cutting the first electroformed member and the second electroformed member, cutting is performed in a region where only the first electroformed member is formed, to form a needle proximal portion, and cutting is performed in a region where the second electroformed member is formed, to form a needle distal portion.

In the method for manufacturing the needle, the electrolyte includes at least nickel sulfamate, boric acid, and nickel chloride, the particles includes at least one selected from the group consisting of silicon carbide, sapphire, diamond, and alumina ceramics, and the first electroformed member and the second electroformed member are formed under electroforming conditions that a current is 1 to 3 A, a voltage is 1 to 3 V, a temperature of the electrolyte is 45 to 70° C., and an energization time is 1 to 20 minutes.

In the method for manufacturing the needle, the energization time to form the first electroformed member is set longer than the energization time to form the second electroformed member.

In the method for manufacturing the needle, the projections have intervals of 0.2 to 100 μm between adjacent top portions thereof, and heights of 0.1 to 50 μm from an external peripheral surface of the second electroformed member.

In the method for manufacturing the needle, the tapered shape is a curved shape along the longitudinal direction.

In the method for manufacturing the needle, the tapered shape is a straight shape along the longitudinal direction.

In the method for manufacturing the needle, the needle is an injection needle.

Effects of the Invention

The needle according to the present invention includes projections having intervals of 0.2 to 100 μm between top portions thereof and a height of 0.1 to 50 μm from the external peripheral surface. With this structure, when the living body is punctured with the needle, because the projections push the skin of the living body, there is a lower probability that the needle contacts the pain spots, and hence pain is reduced.

In addition, according to a method for manufacturing the needle of the present invention, the external peripheral surface of the needle tube is formed in a tapered shape along the longitudinal direction, and the flow resistance in injection of a liquid medicine into the needle tube is reduced. Besides, the needle tube is formed using an electrolyte with added particles of a certain particle size. This structure enables manufacturing of the needle having projections that reduce pain on the external peripheral surface at low cost with high accuracy.

DESCRIPTION OF THE PREFERRED EMBODIMENTS

<Structure of Needle>

Figure 1A:
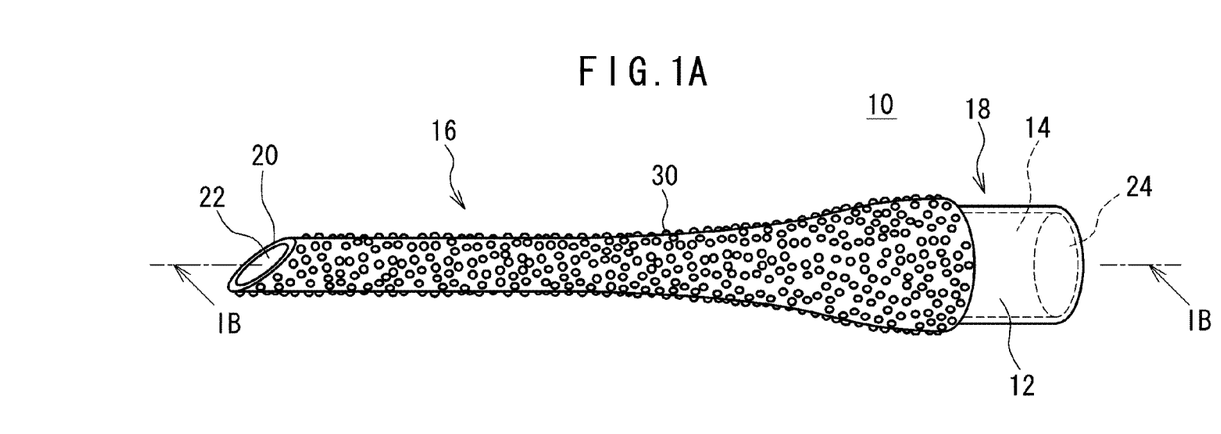
FIG. 1A is a perspective view of a needle according to a present embodiment.
Figure 1B:
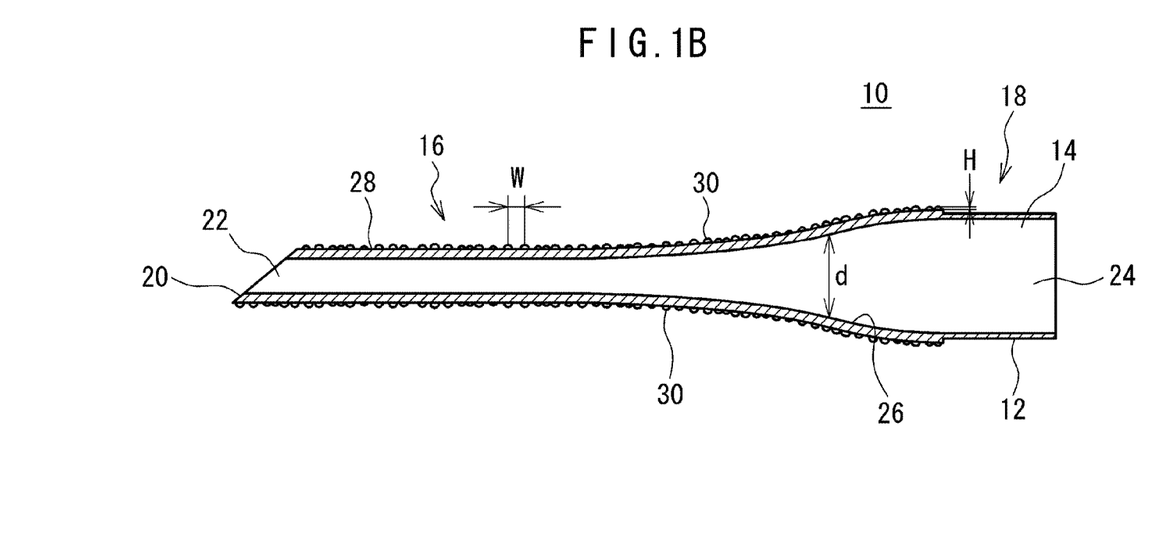
FIG. 1B is a cross-sectional view taken along line IB-IB of FIG. 1A.

FIG. 1A is a perspective view of a needle 10 according to the present embodiment, and FIG. 1B is a cross-sectional view taken along line IB-IB of FIG. 1A. In the present embodiment, the needle 10 is an injection needle that injects a liquid medicine into the living body.

The needle 10 includes a needle tube 12 having a tapered shape and formed by electroforming. The needle tube 12 is provided with a passage 14 having a circular cross section and through which a liquid medicine passes. The needle tube 12 includes a needle distal portion 16 and a needle proximal portion 18. The needle distal portion 16 includes a puncture surface 20 that is cut in an acute-angled shape and a liquid medicine outlet 22. The needle proximal portion 18 includes a liquid medicine injection port 24 that is cut perpendicularly to the axis of the needle tube 12. An internal peripheral surface 26 of the needle distal portion 16 has a curved and tapered shape along the longitudinal direction of the needle tube 12. A diameter d of the passage 14 gradually increases from the liquid medicine outlet 22 toward the liquid medicine injection port 24. In the same manner, an external peripheral surface 28 of the needle distal portion 16 has a curved and tapered shape along the longitudinal direction of the needle tube 12. The external peripheral surface 28 of the needle distal portion 16 is provided with a large number of projections 30. An interval W between top portions of the adjacent projections 30 is 0.2 to 100 μm. A height H of each of the projections 30 from the external peripheral surface 28 is 0.1 to 50 μm.

<Structure of Manufacturing System>

Figure 2:
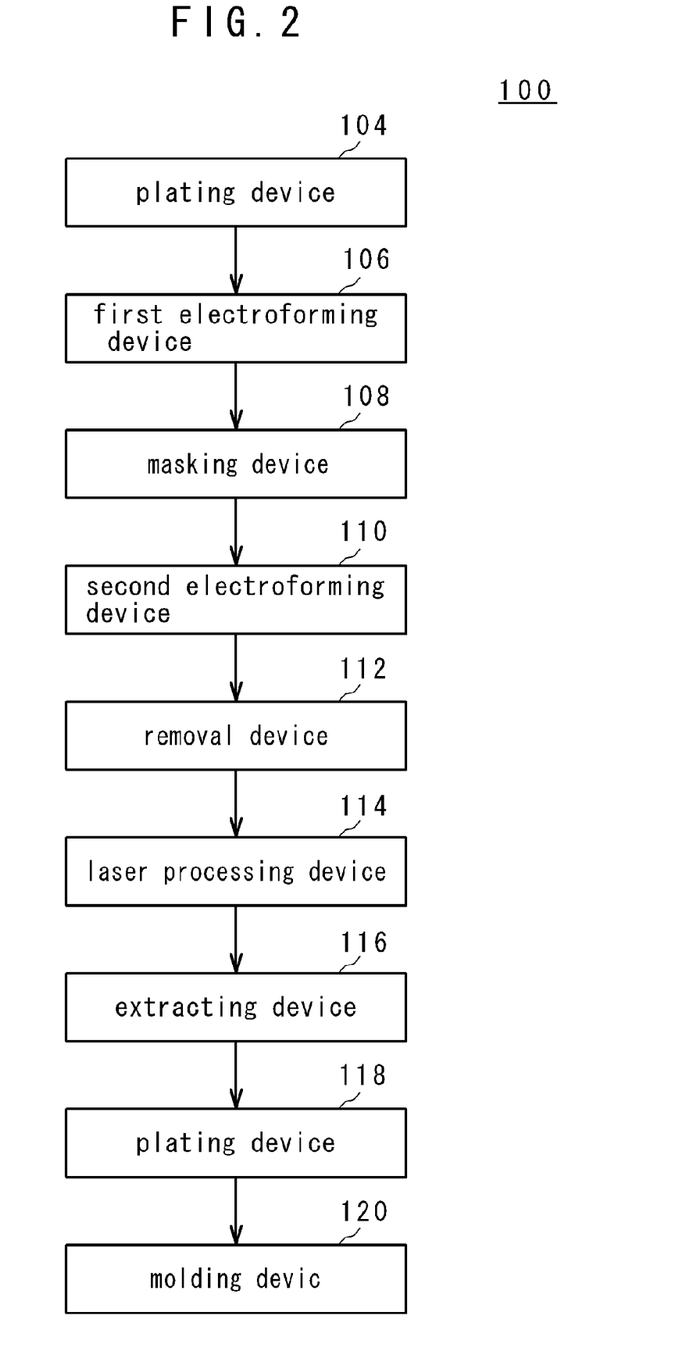
FIG. 2 is a block diagram illustrating a manufacturing system for manufacturing the needle of the present embodiment.
Figure 3:
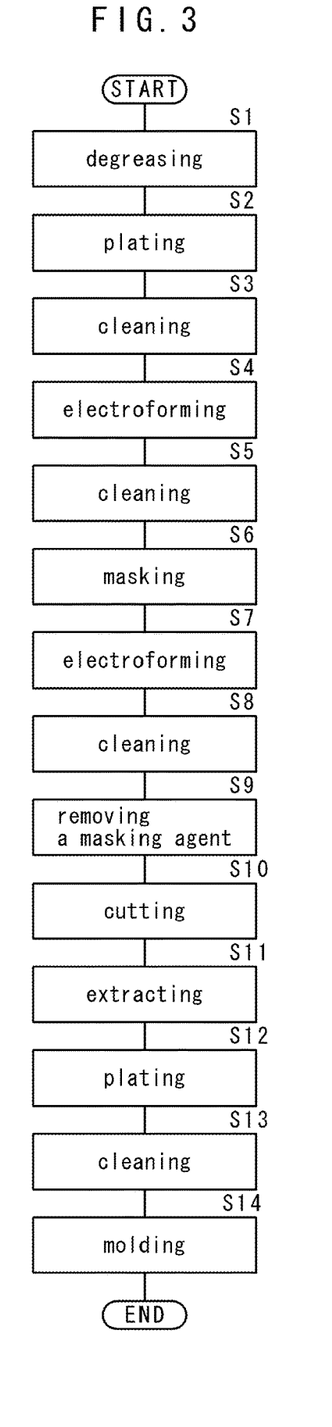
FIG. 3 is a flow chart illustrating a method for manufacturing the needle according to the present embodiment.
Figure 4:
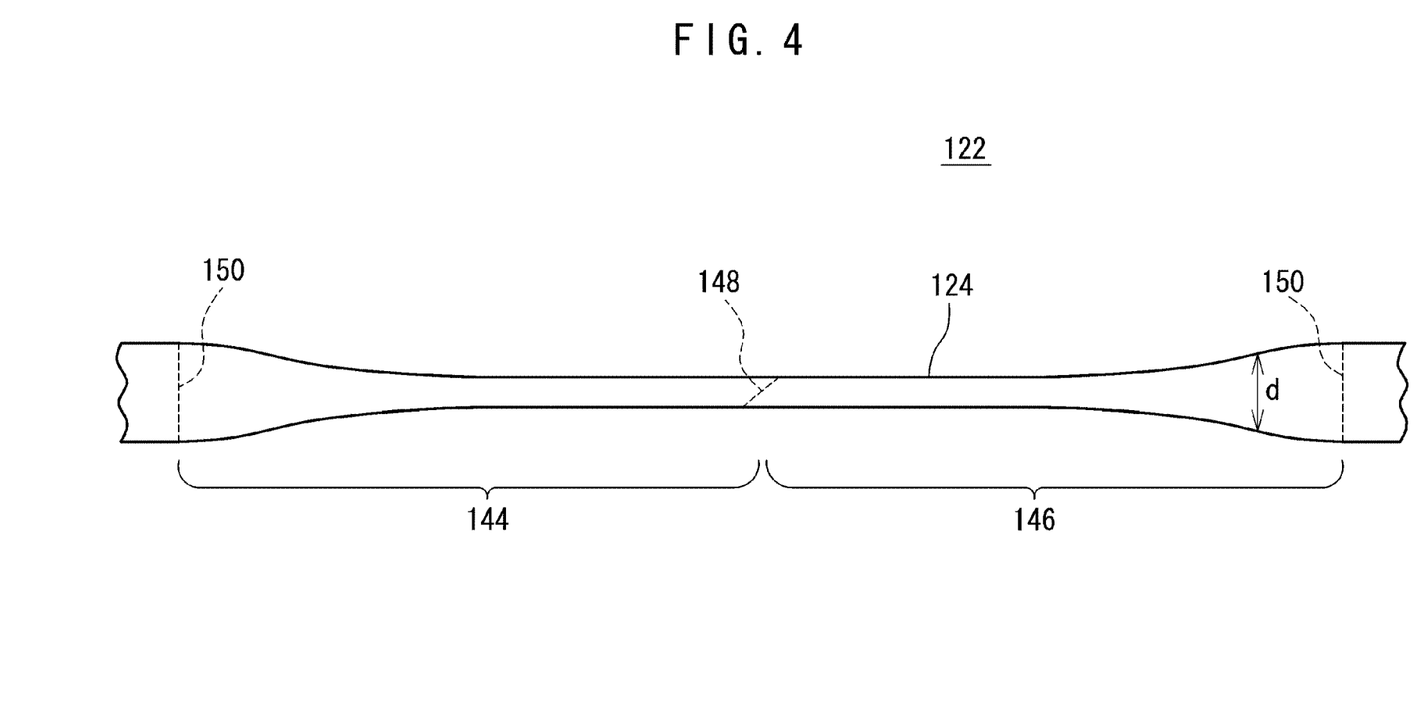
FIG. 4 is a side view of a core material used for manufacturing the needle according to the present embodiment.
Figure 5A:
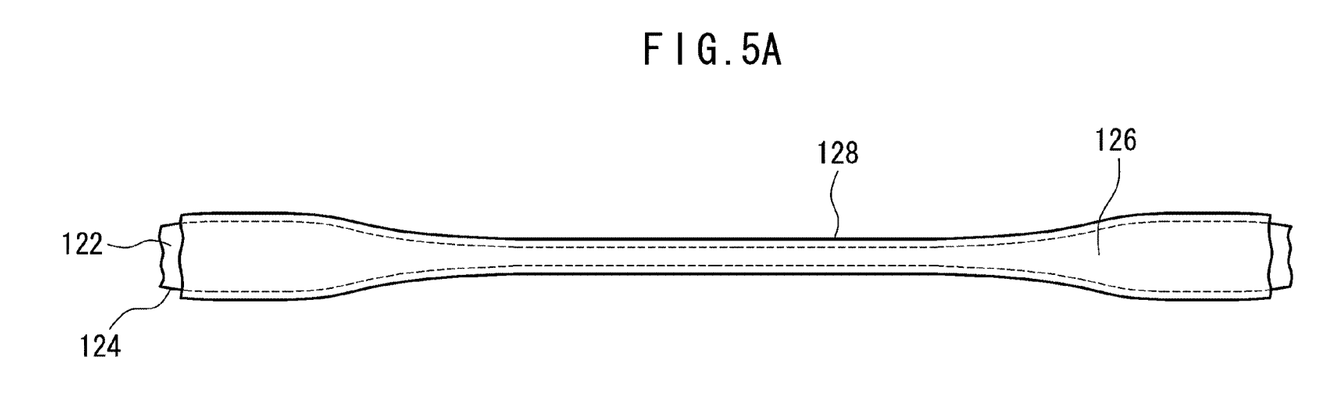
FIG. 5A and FIG. 5B are explanatory drawings illustrating a manufacturing step and a masking step for a first electroformed member in the present embodiment.
Figure 5B:
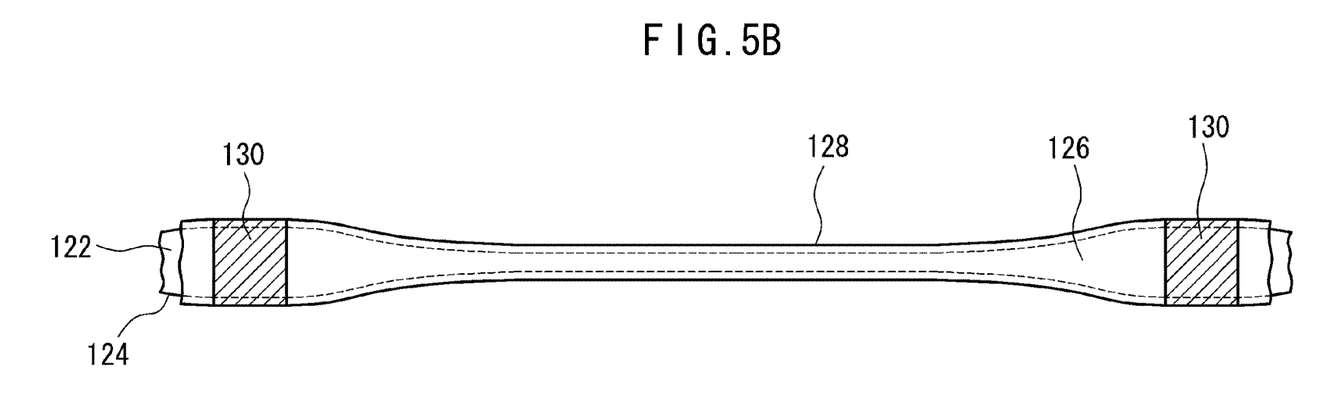
Figure 6A:
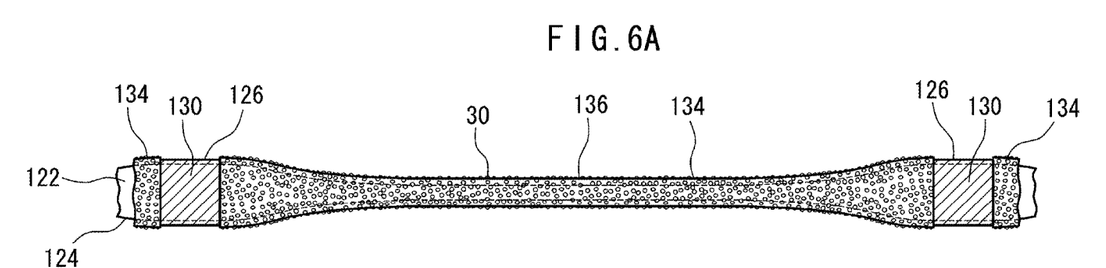
FIG. 6A to FIG. 6C are explanatory drawings of steps from a manufacturing step for a second electroformed member to a manufacturing step for the needle according to the present embodiment.
Figure 6B:
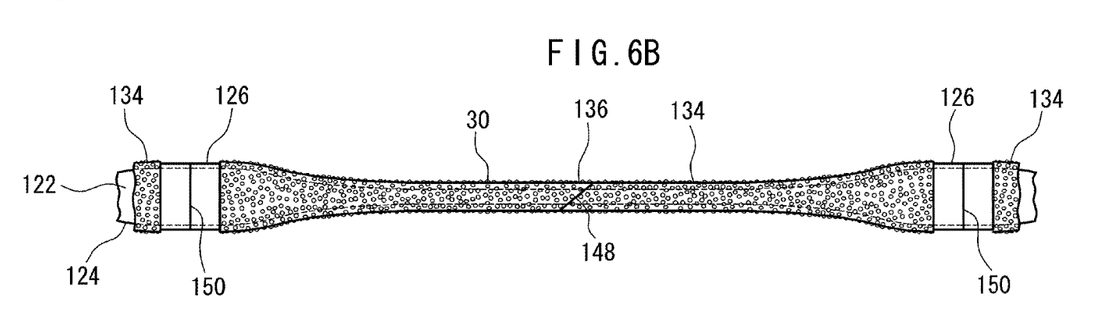
Figure 6C:
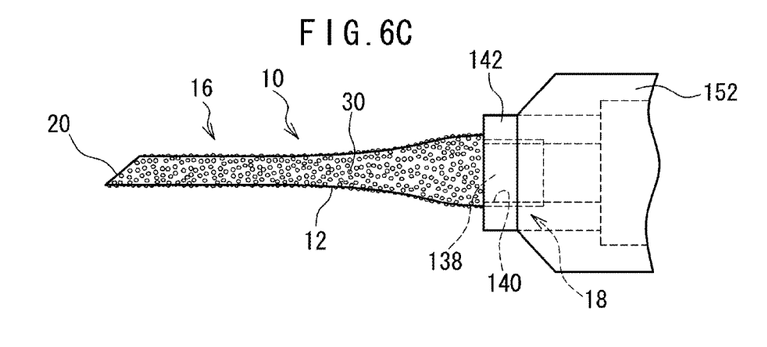

FIG. 2 is a block diagram of a manufacturing system 100 for manufacturing the needle 10 of the present embodiment. FIG. 3 is a flow chart illustrating a method for manufacturing the needle 10 according to the present embodiment. FIG. 4 is a side view of a core material 122 used for manufacturing the needle 10 according to the present embodiment. FIG. 5A and FIG. 5B are explanatory drawings illustrating a manufacturing step and a masking step for a first electroformed member in the present embodiment. FIG. 6A to FIG. 6C are explanatory drawings of steps from a manufacturing step for a second electroformed member to a manufacturing step for the needle according to the present embodiment.

The manufacturing system 100 includes a plating device 104, a first electroforming device 106, a masking device 108, a second electroforming device 110, a removal device 112, a laser processing device 114, an extracting device 116, a plating device 118, and a molding device 120.

The plating device 104 deposits gold on an external peripheral surface 124 of the core material 122 forming the passage 14 of the needle tube 12, to plate the external peripheral surface 124 with gold. The first electroforming device 106 forms a first electroformed member 126 obtained by depositing nickel on the gold-plated external peripheral surface 124 of the core material 122. The masking device 108 applies a masking agent 130 at predetermined intervals on an external peripheral surface 128 of the first electroformed member 126 along the longitudinal direction of the first electroformed member 126. The second electroforming device 110 forms a second electroformed member 134 by depositing nickel on a part of the external peripheral surface 128 of the first electroformed member 126 on which the masking agent 130 is not applied. The second electroformed member 134 includes the projections 30. The removal device 112 removes the masking agent 130 from the external peripheral surface 128 of the first electroformed member 126. The laser processing device 114 irradiates the first electroformed member 126 and the second electroformed member 134 with a laser beam, to cut the first electroformed member 126 and the second electroformed member 134 into a predetermined length and shape. The extracting device 116 extracts the core material 122 from the first electroformed member 126. The plating device 118 deposits gold on the external peripheral surface 128 of the cut first electroformed member 126, the external peripheral surface 136 of the cut second electroformed member 134, and the internal peripheral surface 140 of a hollow portion 138 to perform gold plating. The molding device 120 molds a resin base 142 at the needle proximal portion 18 of the needle 10 formed of the gold-plated first electroformed member 126 and the second electroformed member 134.

<Method for Manufacturing Needle 10>

A method for manufacturing the needle 10 will be explained hereinafter with reference to FIG. 3 to FIG. 6.

First, a core material 122 having a shape corresponding to the passage 14 of the needle 10 is prepared (FIG. 4). The shape of the external peripheral surface 124 in ranges 144 and 146 of the core material 122 is point-symmetrical with respect to the center of a cut surface 148. The external peripheral surface 124 has a curved tapered shape along the longitudinal direction. Broken lines indicates cut surfaces 148 and 150 produced by the laser processing device 114. The diameter d of the core material 122 gradually increases from the cut surface 148 toward the cut surfaces 150. The core material 122 is formed of, for example, stainless. The core material 122 is immersed in a non-ferrous alkaline detergent of 50 g/L and degreased (Step S1).

In the plating device 104, gold is deposited on the external peripheral surface 124 of the degreased core material 122, and the core material 122 is plated with gold (Step S2). The core material 122 is cleaned, and the plating solution is removed from the core material 122 (Step S3).

In the first electroforming device 106, the gold-plated core material 122 is immersed in an electrolyte, and a first electroformed member 126 is formed on the external peripheral surface 124 of the core material 122 under certain electroforming conditions (Step S4, FIG. 5A).

The electrolyte at least includes 450 g/L of nickel sulfamate, 20 to 30 g/L of boric acid, 10 to 20 g/L of a nickel chloride, 5 to 10 cc/L of a sulfonate benzoate imide salt, and 5 to 10 cc/L of saccharin. The electrolyte may also include a sodium lauryl sulfate supersaturated solution, a hardening agent (NSF-E (Nippon Chemical Industrial Co., Ltd.)), sodium naphthalene sulfonate, acetyl cyanamide, Thiourea, and para-tluenesulfonamide. The electrolyte including these substances enables reduction in time required for electroforming. As the certain electroforming conditions, the voltage is 1 to 3 V, the current is 1 to 3 A, the energization time is 1 to 20 minutes, and the temperature of the electrolyte is 45 to 70° C.

In the first electroforming device 106, the core material 122 of a cathode is energized, and the nickel material including sulfur of an anode is energized. The nickel material including sulfur easily dissolves into the electrolyte. The nickel material is formed of, for example, nickel spheres. The nickel spheres are contained in a titanium wire netting. When a voltage of 1 to 3 V and a current of 1 to 3 A are applied between the cathode and the anode, nickel in the anode is ionized and dissolves into the electrolyte. The nickel ions in the electrolyte are deposited as nickel on the core material 122 of the cathode. As a result, the first electroformed member 126 of nickel is formed on the external peripheral surface 124 of the core material 122. The first electroformed member 126 is cleaned, and the electrolyte is removed from the first electroformed member 126 (Step S5).

In the masking device 108, the masking agent 130 is applied at predetermined intervals on the external peripheral surface 128 of the first electroformed member 126 along the longitudinal direction of the first electroformed member 126 formed on the core material 122 (Step S6, FIG. 5B). The regions on which the masking agent 130 of the first electroformed member 126 is applied are portions corresponding to the needle proximal portion 18 of the needle 10 illustrated in FIG. 1A and FIG. 1B.

In the second electroforming device 110, an electrolyte is prepared by including particles of a certain grain size in the electrolyte of the first electroforming device 106. The electrolyte of the second electroforming device 110 may include a sodium lauryl sulfate supersaturated solution, a hardening agent (NSF-E (Nippon Chemical Industrial Co., Ltd.)), sodium naphthalene sulfonate, acetyl cyanamide, Thiourea, and para-tluenesulfonamide. In the same manner as in Step S4, the electrolyte including these substances enables reduction in time required for electroforming. The particles included in the electrolyte includes at least one selected from the group consisting of silicon carbide, sapphire, diamond, and alumina ceramics. The grain size of the particles is 0.2 to 100 μm. The concentration of the particles in the electrolyte is, for example, approximately 10 g/L in the case of sapphire.

In the second electroforming device 110, the first electroformed member 126 with the applied masking agent 130 is immersed in the electrolyte, and the second electroformed member 134 is formed on the part of the external peripheral surface 128 of the first electroformed member 126 that is not masked, under certain electroforming conditions (Step S7, FIG. 6A). As the certain electroforming conditions, the voltage is 1 to 3 V, the current is 1 to 3 A, the energization time is 1 to 20 minutes, and the temperature of the electrolyte is 45 to 70° C. The energization time is set shorter than the energization time for forming the first electroformed member 126. Accordingly, the second electroformed member 134 is formed with a thickness smaller than the thickness of the first electroformed member 126, and with a shorter time.

The cathode and the anode of the second electroforming device 110 are formed in the same manner as the cathode and the anode of the first electroforming device 106. When a current of 1 to 3 A with a voltage of 1 to 3 V is applied between the cathode and the anode, nickel in the anode is ionized and dissolves into the electrolyte. The nickel ions in the electrolyte are deposited as nickel on the first electroformed member 126 of the cathode. As a result, the second electroformed member 134 of nickel including the particles is formed on the part of the external peripheral surface 128 of the first electroformed member 126 on which the masking agent 130 is not applied. The projections 30 of the particles included in the electrolyte is formed on the external peripheral surface 136 of the second electroformed member 134. No second electroformed member 134 is formed on the external peripheral surface 128 of the first electroformed member 126 with the applied masking agent 130. The second electroformed member 134 is cleaned, and the electrolyte is removed from the second electroformed member 134 (Step S8).

The interval W between the top portions of the adjacent projections 30 formed on the external peripheral surface 136 of the second electroformed member 134 is easily controlled according to the concentration of the particles included in the electrolyte and the energization time. In addition, the height H of the projections 30 from the external peripheral surface 136 (corresponding to the external peripheral surface 28 of the needle 10) of the second electroformed member 134 is easily controlled according to the grain size of the particles included in the electrolyte. The external peripheral surface 136 of the second electroformed member 134 is provided with projections 30 with the interval W of 0.2 to 100 μm and the height H of 0.1 to 50 μm.

In the removal device 112, the masking agent 130 applied in Step S6 is removed from the external peripheral surface 128 of the first electroformed member 126 (Step S9).

In the laser processing device 114, the first electroformed member 126 and the second electroformed member 134 are cut into a predetermined length and shape, in accordance with the size (length) of the needle 10 and the shape of the puncture surface 20 (Step S10, FIG. 6B). Specifically, in the laser processing device 114, the cut surface 148 in the center of the second electroformed member 134 provided with the projections 30 is formed in an acute-angled shape, in accordance with the shape of the puncture surface 20 of the needle 10. In addition, in the laser processing device 114, the cut surface 150 in the center of the first electroformed member 126 without the projections 30 is formed at right angles to agree with the shape of the liquid medicine injection port 24.

In the extracting device 116, the core material 122 is extracted from the first electroforming member 126 (Step S11). Extraction of the core material 122 forms a hollow portion 138 corresponding to the passage 14 of the needle 10 (FIG. 6C).

In the plating device 118, gold plating is performed on the external peripheral surface 128 of the first electroformed member 126, the external peripheral surface 136 of the second electroformed member 134, the internal peripheral surface 140 of the hollow portion 138, and the cut surfaces 148 and 150 (Step S12). The first electroformed member 126 and the second electroformed member 134 are subjected to cleaning, and the plating solution is removed therefrom (Step S13), to obtain the needle 10. The main reason for plating the first electroformed member 126 and the second electroformed member 134 with gold is to prevent an allergic reaction in the living body to the nickel forming the needle 10.

In the molding device 120, the base 142 formed of resin is formed as one unitary piece with the needle proximal portion 18 of the needle 10 (Step S14, FIG. 6C). In this case, no projections 30 are formed on the external peripheral surface 128 of the first electroformed member 126 serving as the needle proximal portion 18. Accordingly, the base 142 is in close contact with the external peripheral surface 128 of the first electroformed member 126. The base 142 integrated with the needle 10 is attached to an injection needle main body 152 that supplies liquid medicine.

Figure 7A:
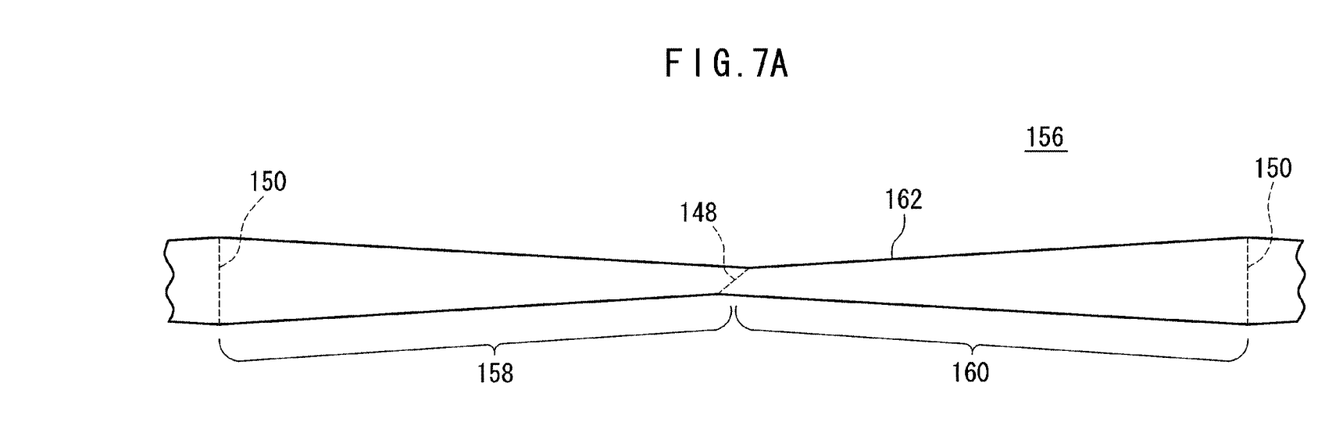
FIG. 7A is a side view of a core material used for manufacturing a needle according to another embodiment.
Figure 7B:
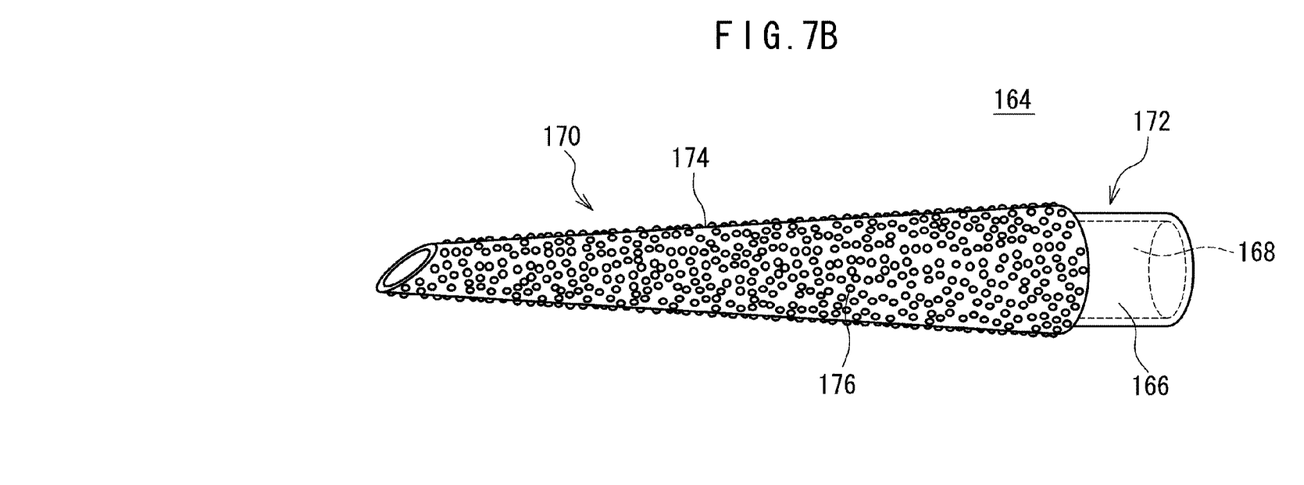
FIG. 7B is a perspective view of the needle manufactured by using the core material of FIG. 7A.

FIG. 7A is a side view of a core material 156 used for manufacturing a needle 164 according to another embodiment, and FIG. 7B is a perspective view of the needle 164 manufactured from the core material 156 of FIG. 7A.

The shape of the external peripheral surface 162 in ranges 158 and 160 of the core material 156 is point-symmetrical with respect to the center of the cut surface 148. The external peripheral surface 162 has a straight tapered shape along the longitudinal direction.

The needle 164 is manufactured using the core material 156, in the same manner as the needle 10. In this case, a passage 168 formed in a needle tube 166 of the needle 164 has a straight tapered shape with a diameter gradually increasing from a needle distal portion 170 toward a needle proximal portion 172. In the same manner, an external peripheral surface 174 of the needle tube 166 has a straight tapered shape with a diameter gradually increasing from the needle distal portion 170 toward the needle proximal portion 172. The external peripheral surface 174 of the needle distal portion 170 is provided with a large number of projections 176, in the same manner as the needle 10.

Because the needles 10 and 164 manufactured as described above are provided with the projections 30 and 176 on the external peripheral surfaces 28 and 174, respectively, for example, when the living body is punctured with the needle 10 or 164, the projections 30 or 176 push the skin of the living body. This structure markedly reduces the probability that the external peripheral surface 28 or 174 contact pain spots. As a result, pain spots are only slightly stimulated by the projections 30 or 176, and this structure markedly reduces pain caused by puncture. In addition, the passages 14 and 168 of the needles 10 and 164 have a curved or straight tapered shape with a diameter gradually increasing from the needle distal portions 16 and 170 toward the needle proximal portions 18 and 172. This structure reduces flow resistance when a liquid medicine is injected into the living body from the needle distal portions 16 and 170. The electroforming step is divided into a step of forming the first electroformed member 126 using an electrolyte including no particles, and a step of forming the second electroformed member 134 using an electrolyte including particles. Accordingly, no projections 30 and 176 are formed on the internal peripheral surfaces 140 of the first electroformed members 126 serving as the passages 14 and 168 of the needles 10 and 164, respectively. Consequently, a liquid medicine can be smoothly injected into the passages 14 and 168. In addition, because the needles 10 and 164 are obtained by cutting the first electroformed member 126 and the second electroformed member 134 into ones of predetermined lengths, a large number of needles 10 and 164 can be manufactured in a short time.

The present invention is not limited to the above embodiments, but can be varied within a range not departing from the gist of the present invention.

The needles 10 and 164 are explained as injection needles in the present embodiment, but the present invention is not limited thereto, as long as the needle is used for puncturing the living body. For example, the needle may be a sampling needle to sample a body fluid from the living body.

The manufacturing process of the present embodiment is a process in which, after the first electroformed member 126 is formed, the masking agent 130 is applied, and thereafter the second electroformed member 134 is formed, but the present invention is not limited thereto, as long as the needle 10 or 164 including the projections 30 or 176 can be formed. For example, as a modification of the manufacturing process, the step of applying the masking agent 130 may be omitted, and, after the first electroformed member 126 is formed, the second electroformed member 134 may be formed on the whole external peripheral surface 128 of the first electroformed member 126. The needle 10 or 164 formed as described above has a structure in which the projections 30 or 176 are formed on the whole external peripheral surface 28, and the base 142 is formed at the needle proximal portion 18 or 172 including the projections 30 or 176.

KEY TO SYMBOL

10,164: needle
12,166: needle tube
14,168: passage
16,170: needle distal portion
18,172: needle proximal portion
20: puncture surface
22: liquid medicine outlet
24: liquid medicine injection port
26,140: internal peripheral surface
28,124,128,136,162,174: external peripheral surface
30,176: projection
100: manufacturing system
104,118: plating device
106: first electroforming device
108: masking device
110: second electroforming device
112: removal device
114: laser processing device
116: extracting device
120: molding device
122,156: core material
126: first electroformed member
130: masking agent
134: second electroformed member
138: hollow portion
142: base
144,146,158,160: range
148,150: cut surface
152: injection needle main body

What is claimed is:

1. A method for manufacturing a needle having a tapered shape along a longitudinal direction by electroforming, the method comprising:
    a step of immersing a core material including an external peripheral surface having a tapered shape along the longitudinal direction in an electrolyte, to form a first electroformed member on the external peripheral surface of the core material;
    a step of immersing the first electroformed member in an electrolyte to which particles of a certain grain size are added, to form a second electroformed member including a plurality of projections on the external peripheral surface of the first electroformed member;
    a step of cutting the first electroformed member and the second electroformed member into a predetermined length, to form a needle including a needle distal portion in an acute-angled shape; and
    a step of extracting the core material from the cut first electroformed member.

2. The method according to claim 1, further comprising:
    a step of applying a masking agent at predetermined intervals on the external peripheral surface of the first electroformed member along the longitudinal direction of the first electroformed member, after the first electroformed member is formed, wherein
    in the step of forming the second electroformed member, the second electroformed member is formed on the external peripheral surface of the first electroformed member on which the masking agent is not applied, and in the step of cutting the first electroformed member and the second electroformed member, cutting is performed in a region where only the first electroformed member is formed, to form a needle proximal portion, and cutting is performed in a region where the second electroformed member is formed, to form a needle distal portion.

3. The method according to claim 2, wherein
    the electrolyte includes at least nickel sulfamate, boric acid, and nickel chloride,
    the particles includes at least one selected from the group consisting of silicon carbide, sapphire, diamond, and alumina ceramics, and
    the first electroformed member and the second electroformed member are formed under electroforming conditions that a current is 1 to 3 A, a voltage is 1 to 3 V, a temperature of the electrolyte is 45 to 70° C., and an energization time is 1 to 20 minutes.

4. The method according to claim 3, wherein the energization time to form the first electroformed member is set longer than the energization time to form the second electroformed member.

5. The method according to claim 3, wherein the projections have intervals of 0.2 to 100 μm between adjacent top portions thereof, and heights of 0.1 to 50 μm from an external peripheral surface of the second electroformed member.

6. The method according to claim 2, wherein the projections have intervals of 0.2 to 100 μm between adjacent top portions thereof, and heights of 0.1 to 50 μm from an external peripheral surface of the second electroformed member.

7. The method according to claim 1, wherein
    the electrolyte includes at least nickel sulfamate, boric acid, and nickel chloride,
    the particles includes at least one selected from the group consisting of silicon carbide, sapphire, diamond, and alumina ceramics, and
    the first electroformed member and the second electroformed member are formed under electroforming conditions that a current is 1 to 3 A, a voltage is 1 to 3 V, a temperature of the electrolyte is 45 to 70° C., and an energization time is 1 to 20 minutes.

8. The method according to claim 7, wherein the energization time to form the first electroformed member is set longer than the energization time to form the second electroformed member.

9. The method according to claim 7, wherein the projections have intervals of 0.2 to 100 μm between adjacent top portions thereof, and heights of 0.1 to 50 μm from an external peripheral surface of the second electroformed member.

10. The method according to claim 1, wherein the projections have intervals of 0.2 to 100 μm between adjacent top portions thereof, and heights of 0.1 to 50 μm from an external peripheral surface of the second electroformed member.

11. The method according to claim 1, wherein the tapered shape is a curved shape along the longitudinal direction.

12. The method according to claim 1, wherein the tapered shape is a straight shape along the longitudinal direction.

13. The method according to claim 1, wherein the needle is an injection needle.

* * * * *